United States Patent [19]
Danne et al.

[11] 3,987,550
[45] Oct. 26, 1976

[54] SYSTEM AND APPARATUS FOR DENTAL PROPHYLAXIS

[76] Inventors: Arthur J. Danne, 13196 E. 6th Place, Aurora, Colo. 80010; Richard A. Edwards, 5340 S. Oak St., Littleton, Colo. 80123

[22] Filed: Apr. 30, 1974

[21] Appl. No.: 465,506

Related U.S. Application Data

[63] Continuation-in-part of Ser. No. 254,330, May 17, 1972, abandoned, which is a continuation of Ser. No. 106,648, Jan. 15, 1971, abandoned.

[52] U.S. Cl. .................................................. 32/59
[51] Int. Cl.[2] .......................................... A61C 3/06
[58] Field of Search ............................ 32/57, 58, 59

[56] References Cited
UNITED STATES PATENTS

| | | | |
|---|---|---|---|
| 2,400,912 | 5/1946 | Britt et al. | 32/26 |
| 2,738,528 | 3/1956 | Fridge | 32/59 |
| 2,838,210 | 6/1958 | Detrie et al. | 222/389 |
| 3,500,824 | 3/1970 | Gilbert | 128/62 A |

*Primary Examiner*—Robert Peshock
*Attorney, Agent, or Firm*—Wm. Griffith Edwards

[57] ABSTRACT

A dental prophylaxis handpiece is provided with a supply conduit through which the prophylaxis material is supplied directly to the center of the rotatable flexible cup or applicator. The configuration and mounting of the cup prevent admission of abrasive material to the bearings. A high pressure fluid actuated control system makes possible a quick-shot or small slug supply of the prophylaxis material by operation of a remote foot operated control. All of the functions of motor control, material supply, water flushing and air drying may be performed by the dentist by actuation of a foot control unit or other suitable actuating device.

27 Claims, 13 Drawing Figures

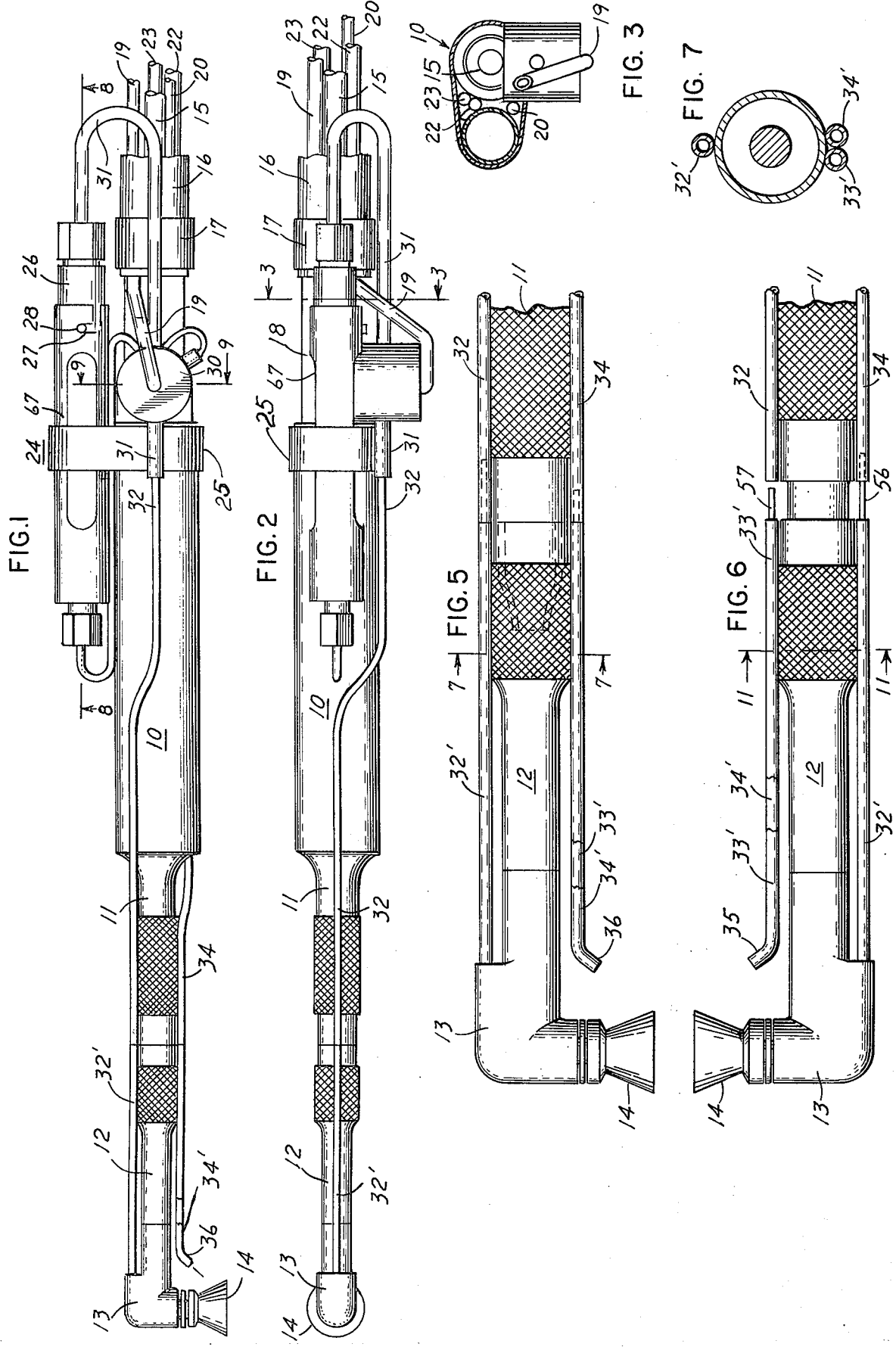

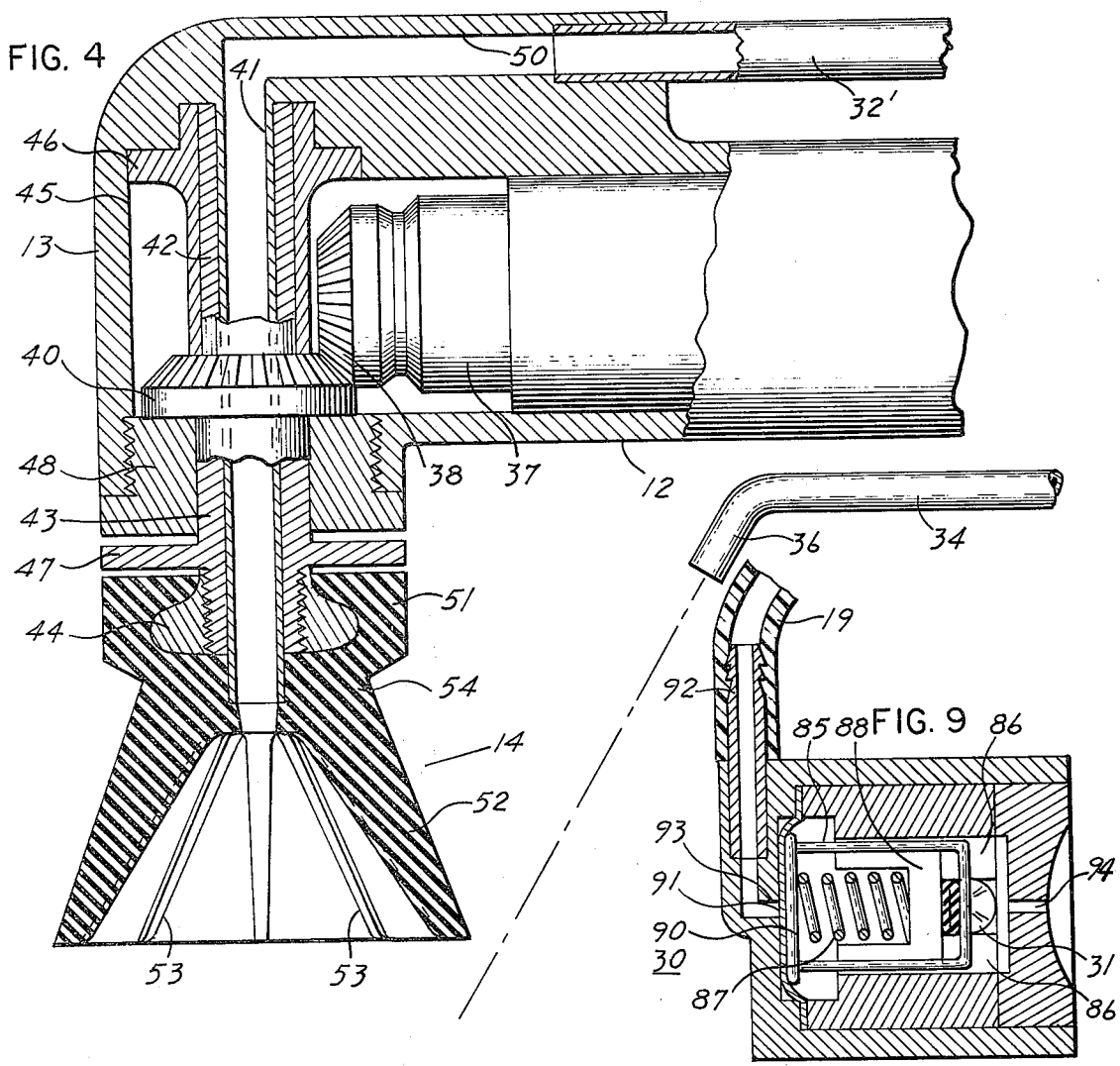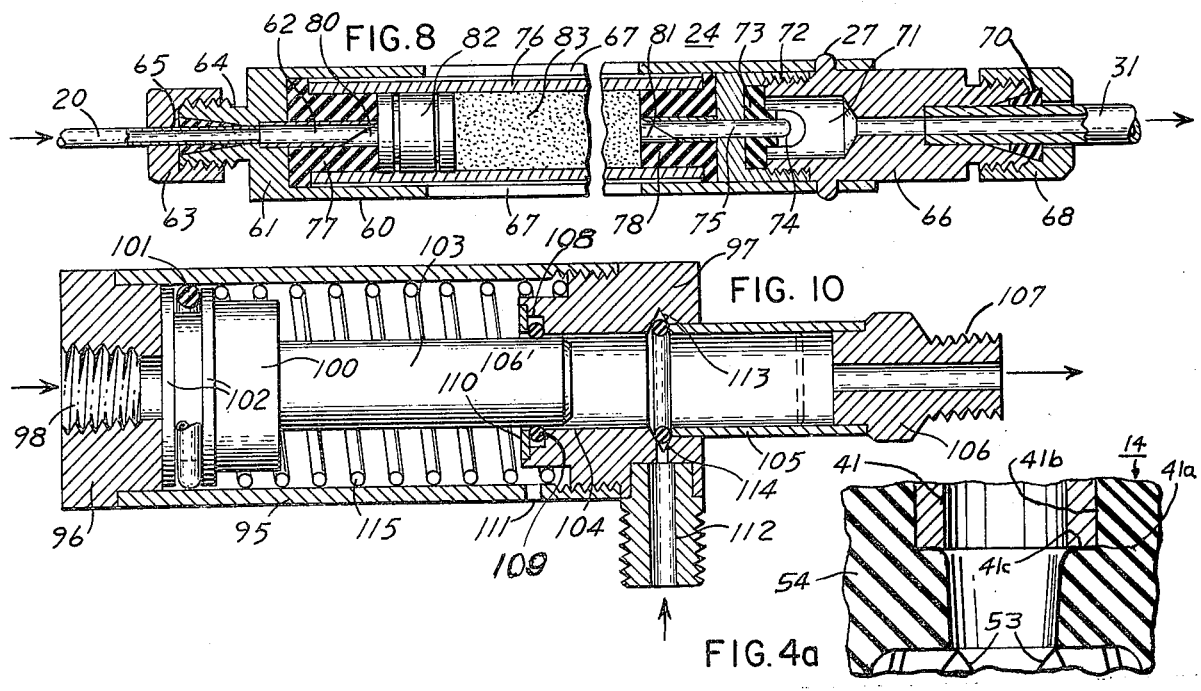

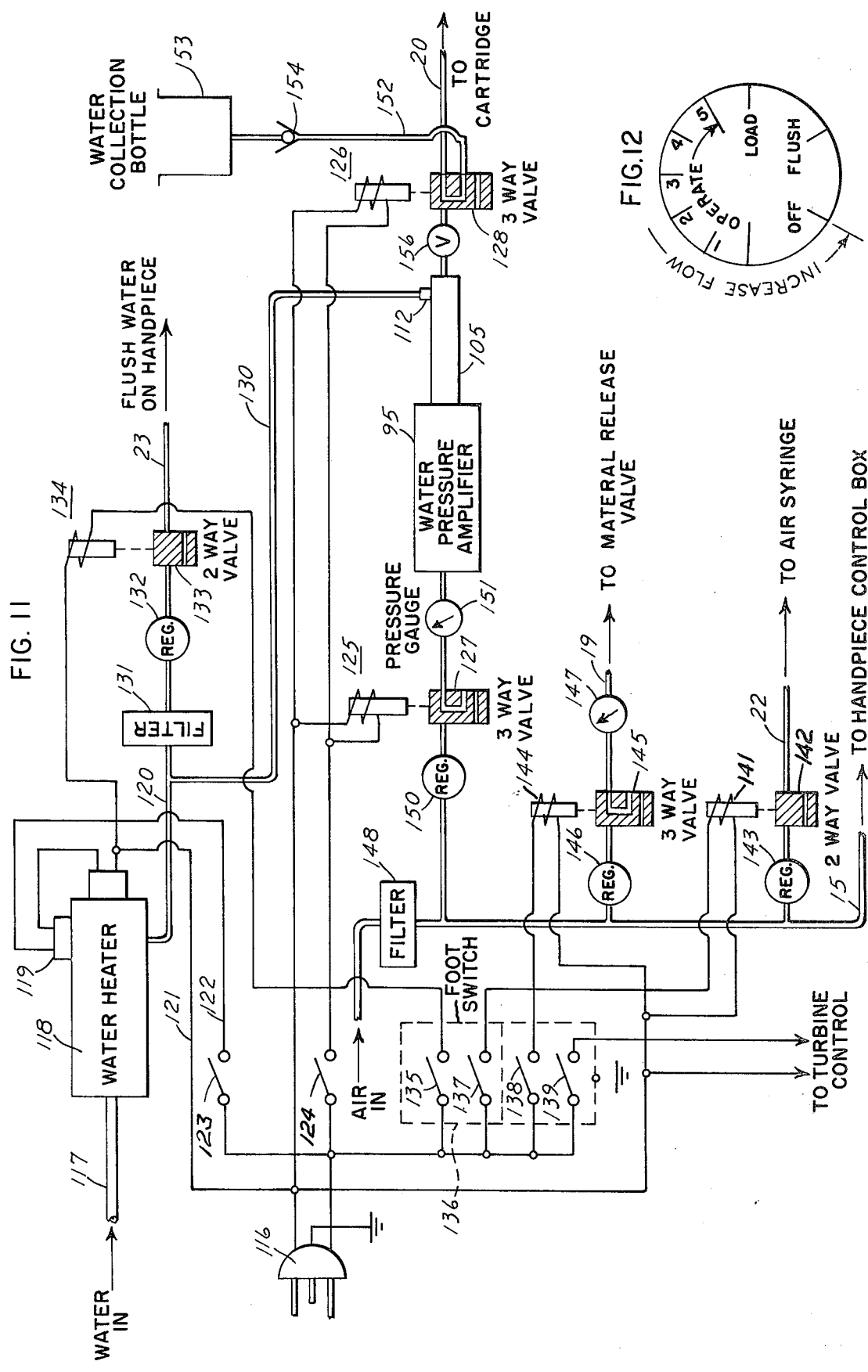

1

SYSTEM AND APPARATUS FOR DENTAL PROPHYLAXIS

This is a continuation-in-part of application Ser. No. 254,330 filed May 17, 1972 and now abandoned, which is a continuation of application Ser. No. 106,648 and now abandoned Jan. 15, 1971.

This invention relates to dental prophylaxis apparatus and particularly to an improved dental handpiece and control system for supplying prophylaxis materiaal or paste to the applicator cup on the handpiece.

In the practice of dental prophylaxis involving the cleaning and polishing of the teeth it has been proposed, heretofore, that the prophylaxis material be supplied from a pressure source directly to the flexible applicator cup. Apparatus for such application of the fluid material has been devised with a view to reducing the time consuming and inconvenient practice of picking up the material from a supply receptacle; this requires back and forth movement of the handpiece between the patient's mouth and the paste receptacle and interrupts the dentist's work. Furthermore, the quantity of paste required at the cup varies during the prophylaxis treatment and it is desirable that the quantity of paste be easily controlled and also that the supply and control of the paste be effected without requiring the dentist to interrupt his work. Accordingly, it is an object of the present invention to provide a dental prophylaxis system including an improved arrangement for minimizing the interruption of the dentist's work during the treatment.

It is another object of this invention to provide an improved apparatus for controlling the supply of prophylaxis material to the applicator cup on a dental handpiece during the use of the handpiece.

It is another object of this invention to provide an improved dental prophylaxis system of the type including a pressurized supply of prophylaxis material for selectively controlling the amount of the material delivered to the applicator cup during the use of the cup in a patient's mouth.

It is a further object of this invention to provide a dental handpiece for prophylaxis treatment utilizing a flexible applicator cup and including an improved arrangement for preventing the admission of the prophylaxis material to the bearing surfaces of the handpiece.

It is a further object of this invention to provide a dental prophylaxis system including an improved control enabling the dentist to perform all treatment functions without changing his hand position or removing the handpiece from the patient's mouth.

Briefly, in carrying out the objects of this invention in one embodiment thereof, a dental prophylaxis system is provided which includes a dental handpiece having a passage for delivering through the head thereof a supply of dental prophylaxis material which flows from the passage into the interior of a flexible applicator cup mounted on the handpiece to be driven thereby. The configuration of the flexible cup and of its mounting on the handpiece are such that the admission of the treatment material to the bearing surfaces of the handpiece is effectively prevented at all times and particularly during the use and distortion of the cup in the course of the treatment. The control system includes air, water and prophylaxis material supplies and selective controls for delivering water, air or material to the patient's mouth during the treatment. The controls are effected by operation of a foot controller and allow the dentist to work without interruption and without shifting the position of his hand on the handpiece. A precise control of the supply of prophylaxis material is efffected by a high pressure hydraulic drive system which enables the dentist to use a tappping or jogging of the foot control to select a range of quantities of material from a very small quantity to a sufficient quantity to fill or overflow the applicator cup. The control also may be actuated to provide a continuous supply of material if desired.

The features of novelty which characterize this invention are pointed out with particularity in the claims annexed to and forming a part of this specification. The invention itself, however, both as to its organization and method of operation, together with further objects and advantages thereof, may be best understood by reference to the following description taken in connection with the accompanying drawings, in which:

FIG. 1 is a side elevation view of a dental handpiece embodying features of the invention;

FIG. 2 is a top plan view of the handpiece of FIG. 1;

FIG. 3 is an end elevation view partly in section of the handpiece of FIG. 1;

FIG. 4 is an enlarged sectional elevational view of the head assembly of the handpiece of FIG. 1;

FIG. 4a is an enlarged view of a portion of the assembly of FIG. 4;

FIG. 5 is an enlarged elevation view of the forward end of the handpiece of FIG. 1;

FIG. 6 is a view similar to FIG. 5 with the front end of the handpiece turned to its flushing position;

FIG. 7 is a sectiional view taken along the line 7—7 of FIG. 5;

FIG. 8 is an enlarged view taken along the line 8—8 of FIG. 1;

FIG. 9 is an enlarged sectional view of aa portion of the handpiece taken along the line 9—9 of FIG. 1;

FIG. 10 is a sectional elevation view of a water pressure amplifier employed with the system of the invention;

FIG. 11 is a schematic diagram of the fluid and electrical ciricuits of the system of the invention; and FIG. 12 is a face view of a flow control dial for the system of FIG. 11.

Referring now to the drawings, the handpiece illustrated in FIGS. 1, 2 and 3 comprises an elongated cylindrical main body portion 10 and a portion 11 of reduced cross section to which is secured a detachable tip 12 having a head 13. A motor (not shown) is arranged within the main body portion 10 and through a drive connection arranged in the portion 11 and the tip 12 rotates a detachable flexible applicator cup 14. In this embodiment, the motor within the main body portion 10 is an air motor or turbine driven by air supplied through a flexible conduit 15 arranged in a main tubing or enclosure 16. An electric motor may also be used in which case the power leads would extend through the tube 16 instead of the motor air supply tube 15. The tubing 16 is secured to the handpiece by a clamping member 17 which fastens the tubing 16 securely to a tubular or channel-like extension 18 extending rearwardly from the body portion 10. In addition to the tubing 15, the tube 16 carries four additional fluid supply tubes 19, 20, 22 and 23 which are fluiid control supplies and drying air and flushing water supplies.

The tube 20 carries high pressure water and is connected to a paste cartridge receiver 24 secured to the main body portion 10 by a clamp 25. A cartridge containing the prophylaxis material or paste is placed within the receiver 24 and locked by a closure member 26 by means of a bayonet joint consisting of pairs of opposite slots 27 and pins 28. Paste is delivered as desired to the interior of the cup 14 by operation of a valve 30 mounted on the handpiece and which is controlled remotely as by a foot operated pedal. The valve is operated by the admission of air through the tubing 19 to the valve 30 whereupon the paste is discharged from the cartridge through a flexible tube 31 passing through the valve 30 and connected to a tubing 32 which is preferably rigid and which is secured on the body portion 10 and the reduced portion 11 of the handpiece. The tubing 32 is detachably connected to a tube 32' on the tip for delivery of the paste to the head 13 and thence to the cup 14. Air and wateer used for drying and flushing purposes are delivered through the tubes 22 and 23, respectively, which are connected to tubes 33 and 34, respectively. If desired, both air and water may be supplied concurrently through the tubes 22 and 23 to produce a water spray. The tubes 33 and 34 are secured to the body 10 and detachably engage respective tube sections 33' and 34' attached to the tip 12 of the handpiece and terminating in angularly directed tips 35 and 36, as shown in FIGS. 5 and 6, respectively.

From the foregoing, it will be observed that all of the functions of the handpiece are accomplished by control or supply fluids passing to the handpiece through the tubes within the tubular casing 16. The casing may be made highly flexible and may be coiled or otherwise arranged in accordance with present day dental equipment practice. The manner in which the system is controlled will be explained below in connection with the description of the fluid and electrical control system. This is a remote control system and all of the functions may be performed by the dentist without changing his hand position on the handpiece and without removing the applicator cup from the working area of the teeth. The prophylaxis material or paste supplied to the cup is employed in the usual manner and at any time that the dentist wishes to flush the working area, water is supplied through the discharge tip 36 and the area can then be dried by supplying air through the tip 35. During the use of the applicator cup 14 while the cup is rotating it is pressed against the surfaces of the teeth and distorted in various directions depending upon the requirements of the work. The cup and its mounting are so constructed that although the paste or prophylaxis material is present near the bearing surfaces of the head 13, it is prevented from reaching these surfaces and damaging the bearings.

The details of construction of the head 13 and the mounting for the cup 14 are illustrated in FIG. 4 wherein the head 13 is shown as constituting a short right angled extension of the detachable tip 12. The applicator cup 14 is rotated by operation of a shaft 36 driven by the motor within the body of the handpiece and which has a beveled gear 38 at its end mounted in engagement with a beveled gear 40. The gear 40 is journaled on a tube 41 illustrated as formed integrally with the material of the head 13 and rotates about this tube as a shaft. The hub assembly of the gear 40 comprises an upper extension 42 and a lower portion 43 terminating in an attaching member illustrated as a threaded end. The attaching member engages a threaded fitting or adapter 44 shown as a head or bead about which the cup 14 is held. The top end of the extension 42 engages the adjacent top wall of a recess 45 provided within the head surrounding the gears 38 and 40. A sleeve or guide bushing 46 is mounted in the top of the recess 45 and acts as an outer bearing or shield for the extension 42. The lower extension 43 is provided with a slinger ring 47 just above the threaded end which serves to throw outwardly any liquid which reaches it and prevents such liquid from flowing onto the bearing surfaces between the extension 43 and a bushing 48 in which it is journaled; the bushing is threadedly secured in the head 13.

The prophylaxis material admitted from the tube 32' enters a pasage 50 extending across the top of the head 13 and terminating in the tube 41 so that the material flows downwardly through the tube 41 and into the cup 14. The cup 14 is made of highly flexible material which is readily deformed but has sufficient resilience to grip and retain itself on the member 44 during the working operation. The cup comprises an upper portion 51 which is shaped to conform to the adapter member 44 but is of slightly smaller dimensions so that it is held securely in place when it is stretched over the adapter. The lower portion of the cup is an outwardly flaring bell 52 formed with internal ribs 53 which facilitate the cleaning operation. A thick central portion 54 of the cup is provided with a cylindrical center passage which is preferably of a uniform diameter substantially less than the outer diameter of the tube 41 so that when the cup is pressed over the bead or threaded on the lower end of the hub assembly the tube 41 extends into the passage for a distance short of the end of the passage. The remaining portion of the passage wall first bends, at least partially, in face engagement with the bottom end surface of the tube and then forms in a substantially conical or tapering configuration due to the stretching of the cup and the contraction of the passage toward its bottom end, the opening at the bottom being of the diameter of the unstretched cylindrical passage. The termination of the end of the tubing 41 so that it lies within the cylindrical passage in the cup 14 provides a characteristic of the mounting whereby the admission of the prophylaxis material to the bearing area of the cup which rotates on the tube 41 is minimized. The lower end of the cylindrical passage in the cup thus provides a rotatable extension of the tube 41. The length of the free passage beyond the tube 41 may be selected over a wide range; it depends upon the characteristic of the material of the cup and its configuration. In some cases the free passage may be very short as compared with that in the illustrated embodiment. It has been found by repeated tests that a flexible cup as illustrated and with the tube extending only partially through the cylindrical center passage operates to prevent admission of the treatment material to the bearing surfaces on the exterior of the tube 41 and that bearing wear due to prophylaxis material is effectively eliminated. Leakage or flow of the material around the portion of the cup engaging the bottom end of the tube 41 is prevented, and, regardless of the pressures and distortions of the cup during operation, the sealing effect is maintained; pressure on the cup as it is presseed against the teeth automatically causes a tighter seal between the end of the tube and the rotating cup. It has been observed that on direct pressure of the cup along the axis of the tube the width of the discharge opening of the cup at the end of the cylindrical portion decreases. These characteristics are maintained regardless of the distortion of the cup; the seal becoming tighter under pressure, either directly along the axis of rotation or at an angle thereto. The construction of the cup and the arrangement of its mounting on the lower end of the tube 41 with a portion of the passage in the cup extending beyond the tube end provides an efffective rotating seal. For purposes of illustration and in contrast to the operation of the cup of the present invention, it has been found that if the end of the tube, such as the tube 41, extends through the cup into the interior thereof, the operation and distortion of the cup allows the admission of the prophylaxis material to the bearing surfaces and quickly destroys these surfaces including those on the tube 41 and drive gears 38 and 40.

The normal life of the angles or heads of motor driven dental handpieces which are used for prophylaxis treatment is short and may, by way of example, be of the order of one thousand treatments or about three months use. The short life of these heads is due to the presence of abrasive substance in the prophylaxis treating material or paste which finds its way into the bearings. When the handpiece is constructed to deliver the material directly to the treatment area through the flexible rubber cup the wear of the angle or head bearings becomes severe and an extremely short life makes these handpieces impractical. The present invention utilizes compression of the flexible applicator cup to form a rotating seal which effectively prevents the abrasive material from reaching and destroying the bearing surfaces for at least as long a time as that in which the normal wear of the head renders it unserviceable. Thus the heads of handpieces which embody the delivery of prophylaxis paste to the treatment area through the handpiece are made usable for the same normal life as the heads of conventional handpieces. The full advantage of the feeding of the paste to the treatment zone is thus realized and the time saving features of direct paste supplying dental handpieces are made fully available.

The manner in which the seal is effected is indicated more clearly in FIG. 4a which is an enlarged view of the area of the seal between the supply tube end and the flexible cup as viewed in FIG. 4. When the flexible cup is pressed over the retaining bead 44 the tube 41 is moved into the central passage of the cup and expands the wall of the passage until the tube is in the position shown, a slightly tapering portion of the cup passage extending beyond the end of the tube as shown. This compresses the rubber tightly about the end of the tube and particularly against the annular shoulder or corner edge. The handpiece drive is then actuated before paste has been applied and the bead 44 is rotated on the tube 41; the cup is rotated about the stationary tube 41 and the right angle corner of the tube, indicaated at 41a, cuts or wears its way into the rubber, and, as the rotation continues, forms an effective seal at the corner which, when the paste is applied, prevents movement of the fluid material around the end of the tube and onto the bearing surface. The seal is formed in two portions: a cylindrical seal 41b about the outer end surface of the tube adjacent the corner and an end face seal 41c in a plane normal to the axis of rotation. During application of pressure and lateral movement of the applicator cup over the treated surface there is a tendency for the hub or central portion 54 of the cup to move laterally over the end surface of the tube 41. The motion produced may, for example, be an eccentric movement of the seal 41c over the end face of the tube; the seal 41c then maintains face engagement with the end face over a sufficient area to maintain its seal and prevent the opening of a passage to the outer cylindrical surface of the tube. The distortion of the cup during use thus is prevented from causing a separation of the seal which would allow paste to flow onto the cylindrical bearing surfaces. Thus each cup or applicator forms its seal when it is positioned on the head and rotated by opeeration of the power drive. The corner of the tube 41 wears slowly and as it becomes rounded the effectiveness of the seal is gradually lost. It has been found, however, that this does not occur before the main bearing of the gear 40 has worn beyond practical usability. By way of example, for some handpieces an average of one thousand or more applicator cups may be used before the angle or head bearing between the gear 40 and the bushing 48 has worn out so that the head must be discarded. The seal formed by each cup in turn when it is applied to the head as described above thus prevents admission of paste to the tube bearing and assures useful operatioon of the head or angle for its full normal life.

By employing the highly flexible applicator cup 14 constructed as illustrated and mounted in the manner indicated in FIG. 4, extended use of the cup without bearing wear is made possible and the dentist may work continuously without difficulty which might otherwise arise where the prophylaxis material allowed to reach the bearing surfaces of the head assembly. The control system of this inventioon has been arranged to make full use of the advantageous construction of the applicator cup assembly.

As shown in FIGS. 5 and 6, the prophylaxis material passage at the tip of the handpiece may be flushed and cleaned by drawing the tip 12 longitudinally away from the reduced position 11 of the handpiece and rotating the tip about 180° so that a small diameter connecting extension 56 of the tube 32' may be inserted in and connected to the flushing water supply tube 34. At the same time, the shorter reduced diameter connecting extension 57 of the tube 34' does not reach or enter the material supply tube 32 diametrically opposite and remains open. With the tip of the handpice in the position indicated in FIG. 6, the flushing water may be supplied to the tube 34 and run until all prophylaxis material has been cleared out of the tubes 32' and 41. Normally, the flexible cup 14 will be removed before starting the flushing operation.

The cartridge holder or receiver 24 for supplying the prophylaxis material under pressure is illustrated in FIG. 8. The cartridge holder comprises a cylindrical shell 60 having a closed end 61 at the center of which is mounted a sharp pointed piercing tube 62 connected in communication with the high pressure water supply tube 20 through a sealed connection comprising a cap 63 threaded onto an extension 64 of the wall 61 and having a sealing gasket 65 for preventing leakage about the tube 20. The other end of the cylinder 60 is open and is provided with a detachable closure member or block 66 which is held in position by the bayonet joint previously described. When the cartridge receiver 24 is to be loaded with a cartridge, the end piece or block 66 is removed and the cartridge placed in the chamber. Longitudinal openings 67 on either side of the cartridge receiver are provided for access to the material cartridge. The end block 66 is connected to the flexible tube 31 by a threaded cap 68 and is sealed by gaskeet 70. The member 66 has an internal chamber 71 closed by a threaded cylindrical cap 72 and sealed by a gasket 73. The gasket 73 is formed with an integral check valve 74 comprising a domeshaped member having a razor slit and extending about the open end of a tube 75 mounted in the cap 72; the tube 75 is a piercing tube for providing communication with the interior of a material cartridge indicated at 76. The check valve 74 allows the prophylaxis material to flow outwardly into the chamber 71 and thence to the tube 31 but prevents backflow.

The cartridge 76 comprises a hollow cylinder having flexible rubber-like plastic ends 77 and 78 which acts as gaskets and are provded with sealing closures or diaphragms near their outer ends which are for sealing their respective central passages indicated at 80 and 81, respectively. Within the space between the ends 77 and 78, there is a piston 82 adjacent the end 77 and a charge of prophylaxis material 83 filling the remainder of the cartridge. When the cartridge has been placed in the holder 24, the end piece 66 is pressed into position, thereby causing both the piercing tubes 62 and 75 to break the seals in their respective ends of the cartridge 76 and place the material in position to be discharged. The discharge of the material from the cartridge is effected by pressure fluid supplied through the tube 20 and which moves the piston 82 to the right to force the material 83 out through the cartridge and into the tube 31. The tube 20 is a tube of very small internal diameter which may be of capillary dimensions and which is arranged to receive high pressure water as the driving force for the piston 82. After the passages within the cartridge have been filled and also the tube 31, the discharge of material from the cartridge is controlled by the valve 30 which, as illustrated in FIG. 9, comprises a spring pressed bail 85 arranged to slide in guides 86 between which passes the tube 31. The bail is pressed to the left as shown in FIG. 9 by a helical compression spring 87 which bears against a retainer 88 resting against the guides 86 and a disc 90 which engages a pressure diaphragm 91. The spring exerts force sufficient to flatten the tubing so that the passage through the tubing is closed and flow of prophylaxis material prevented.

When the valve is to be actuated, pressure is admitted through the line 19 which is connected to the valve by a nipple 92 and provides communication with a central passage 93 thereby pressurizing the chamber to the left of the diaphragm and pressing the diaphragm to the right to release the bail 85. The chamber within the valve housing is maintained at atmospheric pressure through a vent 94 in the right hand end of the valve 30. Thus, the diaphragm is free to move the bail when pressure is admitted to the control chamber on its left.

In order to provide adequate high pressure for discharging the prophylaxis material from a cartridge within the holder 24, a pressure amplifier is provided. This amplifier is illustrated in FIG. 10 and comprises a cylinder 95 having a left end closure member 96 welded or otherwise suitably bonded to the cylinder 95 and a right end closure or fitting 97 threadedly attached to the cylinder 95 to afford access to the interior for adjustment or repair. A threaded inlet passage 98 in the closure 96 communicates with the interior of the cylinder 95 on the left hand side of a piston 100 which is provided with an O-ring gasket or seal 101 held between a pair of annular rings 102 formed integrally with the piston 100. A reduced cylindrical section 103 of the piston 100 comprises a small diameter high pressure piston operating in a cylinder 104 formed within the end fitting 97, which constitutes a cylinder block, the cylinder 104 being extended by a cylindrical member 105 which is closed by a fitting 106 terminating in a threaded connection 107. The piston 103 is sealed with respect to the walls of the cylinder 104 by an O-ring 109 retained in an annular recess 108 formed in the left hand end of the fitting 97 and closed by a ring 110 welded or otherwise securely held thereto. The chamber within the cylinder 95 to the right of the piston 100 is vented to the atmosphere through an opening indicated at 111. High pressure water to be supplied to the capillary tube 20 is admitted to the cylinder 104 through an inlet passage 112 which enters an annular recess 113 of triangular cross section in the inner walls of the cylinder block 97 and confines an O-ring 114 which constitutes a check valve. In order to actuate the amplifier, air under pressure is admitted through the connection 98 to the cylinder 95 on the left hand side of the piston 100 and moves the piston 103 forward in the cylinder 104. As it moves forward, the pressure of the water closes the passage to the inlet 112, the O-ring 114 expanding agaiinst the wall of the annular groove 113 for this purpose; as the piston moves forward it supplies water under high pressure as required until the piston reaches the end of its stroke, indicated by dotted lines, or until the charge of material in the cartridge 76 has been exhausted. Piston 100 may be returned to its left hand position in any suitable manner and a compression spring 115 may be provided for this purpose. The spring is not essential as the pressure of the water from the source connected to the inlet 112 will move the piston to the left when the air pressure is released from the left hand end of the piston 100. On the return stroke, water flows from the source through the passage 112, the O-ring 113 acting as a check valve and upon full retraction the piston is ready again for movement to the right and air pressure is admitted to the inlet passage 98 for this purpose. The pressure amplifier provides water under high pressure for passage through the capillary tube 20 and propulsion of the prophylaxis material from the supply cartridge 76. The tube 20 which carries the high pressure water to the prophylaxis material propelling device may be a tube of any suitable material of sufficient strength to carry the required high pressure.

The controller and regulating system for the supply of fluids to the handpiece is shown in FIG. 11. The system is prepared for operation by inserting an electrical plug 116 in a suitable three-terminal socket to connect the system to the power main and to ground. The control system includes a water inleet 117 to provide a supply of water for a heater 118 and thence to supply the water utilizing circuits through a conduit 120. The water heater is heated electrically, current being supplied through lines 121 and 122 upon closing of a switch 123 in the line 122. A suitable thermostatic control 119 is provided to maintain the desired water temperature. Closing of the switch 124 connects solenoids 125 and 126 to be energized thereby moving two position valves 127 and 128 from their lower or U-turn positions to their upper or straight through positions. These are three-way valves and control the supply of air to the water pressure amplifier 95 and the supply of water from the amplifier to the high pressure line 20. Water is supplied from the line 120 to the inlet 112 to the cylinder 105 to the water amplifier through a line 130.

When the pressure amplifier applies high pressure water through the tube 20 to the piston 82 of the cartridge 76 prophylaxis material 83 is expelled from cartridge 76 through line 31. The displaced prophylaxis material 83 on the right side of the piston 82 is replaced by the water supplied by the tube 20 on the left side of piston 82. The pressures in line 20 and line 31 and their respective central passages 80 and 81 are equal. Whenever the expulsion of prophylaxis material 83 is stopped, the check valve 74 prevents back flow of prophylaxis material from tube 31 to the cartridge 76 through the passage 81. When solenoid valve 128 is moved to its release or U-turn position, water under high pressure in the cartridge 76 to the left of the piston 82 is released through line 20 to the U-turn passage of solenoid valve 128 in a manner described below. This reduction in water pressure to atmospheric pressure to the left of the piston 82 allows the prophylaxis material 83 under high pressure to force the piston 82 to the left only slightly resulting in atmospheric pressure on prophylaxis material in the cartridge 76. Thus when the water to the left of the piston 83 and the prophylaxis material to the right of the piston 83 are at atmospheric pressure, the cartridge 76 can be removed without expelling any remaining prophylaxis material from cartridge 76 through the connecting passage 81 or expelling water through the connecting passage 80. The seals 77 and 78 close on removal of the cartridge 76 and prevent any gravity release of water and prophylaxis material through the passages 80 and 81 respectively. Thus the cartridge 76 can be placed in the cartridge holdeer 24 and the prophylaxis material 83 in the cartridge 76 can be used in whole or in part and the cartridge 76 removed and discarded in a clean and efficient manner.

Water for supply to the line 23 flows from line 120 through a filter 131, a pressure regulator 132, and a normally closed two position on-off valve 133. The valve 133 is actuated by a dolenoid 134 which is energized on closing of a switch 135 in a foot control switch assembly 136, upon opening of the valve water flows through the line 23 for flushing and irrigating the mouth.

The foot control 136 indicated diagrammatically in FIG. 11 is of a type generally employed with dental equipment and may be of any suitable construction; the control is arranged so that the operator may actuate any one or more of switches 135, 137, 138 and 139, depending upon the operation or operations which he is performing. Closing the switch 137 energizes a solenoid 141 to open a normally closed two way on-off valve 142 and supply air to the line 22 at a pressure determined by the setting of a regulator 143. The closing of the switch 138 energizes a solenoid 144 to open a valve 145 and supply air under pressure to the line 19 which actuates the prophylaxis paste release valve 30. The pressure in line 19 is controlled by a regulator 146 and is indicated by a gauge 147. When the solenoid 144 is released the valve 145 is in its lower position and connects the line 19 through the U-passage in the valve to the atmosphere for release of pressure. Closing of the switch 139 energizes the air turbine control which in accordance with the present practice is usually located adjacent to the dental chair; the control includes an arrangement for adjustment of the speed of the motor. The air for the turbine is supplied to the handpiece control box or panel through a line 15', and the turbine control on the console provides for selection of the turbine speed. The details of the turbine speed control are not illustrated as they are not essential to an understanding of the present invention. The turbine control on the console supplies air directly to the line 15 at the required pressure for the selected condition of operation. All air supplied to the control system is cleaned by a filter 148. The air supplied to the water pressure amplifier through the valve 127 is at a pressure controlled by a regulator 150 and indicated by a pressure gauge 151. When the valve 127 is in its lower position, as illustrated in the drawing, the air pressure in the water pressure amplifier 95 is atmospheric, it being released through the U-passage in the valve. In a similar manner, the valve 128 in its lower position, as shown in the drawing, connects the water pressure line 20 to a conduit 152 to deliver the excess water to a reservoir 153, a check valve 154 being provided in the line 152. The pressure in line 20 is thus released whenever the solenoid 126 of the valve 128 is de-energized.

The volume of the water delivered through the tube 20 may be controlled by operation of a valve 156 connected between the water pressure chamber 105 and the three-way valve 128. The valve 156 is an adjustable valve and, for example, may be a needle valve; for convenience in selecting the pressure at the valve outlet, the valve is provided with an indicating dial shown in FIG. 12. On this dial there are indicated five pressure positions, a LOAD position and a FLUSH position, the extreme position on turning the valve clockwise being the OFF position. As the valve is turned, it moves from the OFF position through the first five positions and then to the LOAD and FLUSH positions in turn. The LOAD position allows a greater flow than any of the five positions and the FLUSH position provides a greater flow than that of the LOAD position. When a cartridge 76 is to be loaded into the holder 24, the switch 124 is opened and the solenoids 125 and 126 are de-energized; the water pressure is thereby released and the line 20 opened to the conduit 152. The cartridge is then placed in the holder 24 and the dial of FIG. 12 set at its LOAD position, whereupon the solenoids 125 and 126 are energized and water is again supplied through the tube 20. In the LOAD position, the water flows at an optimum rate to allow prophylaxis material to flow through the tube 31 to the valve 30 when the valve 30 is open, whereupon the material passes through the tubes 32 and 32', and thence through the passage 50 to the applicator cup 14. The valve 156 is then set at one of the five operating positions indicated on the dial and the prophylaxis treatment is given the patient. Upon completion of the treatment, the head of the handpiece may be flushed as described heretofore. Thereafter loading requires only the filling of the passages in tubes 32' and 41 to ready the handpiece for further use.

When it is desired to flush the entire handpiece system, the piston 82 in a cartridge 76 is removed from the cartridge, and the cartridge is returned to the handpiece. The dial of the valve 156 is then turned to the FLUSH or high volume water position, the valve 30 and the solenoid valve 128 are opened, and water then flows continuously from the conduit 130 through the inlet passage 112 to the valve 156 and the entire prophylaxis material handling conduits of the system are thereby flushed with water for as long a period as desired.

The action of the system to release prophylaxis material by operation of the valve 30 is such that by tapping the foot switch 138 a very small supply or short of the prophylaxis material may be admitted to the applicator cup 14, the action being such that the bail 85 in the valve 30 may be released for a brief moment. When the bail is returned to its spring biased position the resulting squeeziing or flattenting of the tube 31 aids the final extrusion of paste on each operation. The amount of paste supplied to the cup 14 may thus be varied from a very small amount to an excess of that required to fill the cup or a continuous flow if desired. The entire control of the supply of the paste is effected by the remote control at the foot switch. By actuation of selected functions of the foot control uniit, the dentist may continue his work without interruption and may clean and polish the teeth, flush them with water, and dry them for inspection as he desires. The turbine or motor is, of course, operated at the desired speed selected at the console and in the usual manner and is energized by remote control. The control system is highly effective and precise in operation and saves substantial time in the use of the prophylaxis equipment. Furthermore, the design of the mounting arrangement for the flexible applicator cup is such that wear of the instrument becomes negligible and interruption of work for replacement of the tip and head of the handpiece is minimized.

We claim:

1. In a dental prophylaxis apparatus of the type having a handpiece including means for supporting a rotatable flexible applicator cup and means for supplying fluid treatment material to the interior of the applicator cup a control system comprising:
   drive means for rotating said cup;
   means connectable to a water supply for receiving water and for amplifying the pressure thereof and having an outlet for the discharge of high pressure water;
   a compressible chamber reservoir for holding a supply of treatment material therein;
   a fluid line for conducting treatment material from said reservoir to the interior of the applicator cup;
   a normally closed valve mounted on said handpiece and connected in said fluid line;
   means connected to the outlet of said amplifying means for utilizing high pressure water for compressing said chamber and forcing treatment maaterial into said line; and
   foot controlled quick acting means for selectively opening and closing said valve for intermittent short periods to charge the applicator cup with selected amounts of fluid treatment material whereby the operator's hands are completely free to manipulate the handpiece without interruption and the applicator need not be removed from the patient's mouth.

2. A dental prophylaxis apparatus as set forth in claim 1 wherein said normally closed valve comprises a length of flexible tubing connected in said fluid line as a portion thereof and biasing means for normally pinching said tubing closed.

3. A dental prophylaxis apparatus of the type having a handpiece including means for supporting a rotatable flexible applicator cup and means for supplying fluid treatment material to the interior of the applicator cup a control system comprising:
   drive means for rotating said cup;
   means connectable to a water supply for receiving water and for amplifying the pressure thereof and having an outlet for the discharge of high pressure water;
   a compressible chamber reservoir for holding a supply of treatment material therein;
   a fluid line for conducting treatment material from said reservoir to the interior of the applicator cup;
   a normally closed valve in said fluid line;
   means connected to the outlet of said amplifying means for utilizing high pressure water for compressing said chamber and forcing treatment material into said line;
   manually controlled quick acting means for selectively opening and closing said valve for intermittent short periods to charge the applicator cup with selected amounts of fluid treatment material;
   said normally closed valve comprising a length of flexible tubing connected in said fluid line as a portion thereof and biasing means for normally pinching said tubing closed; and
   said biasing means comprising a compression spring, a rigid stop member, and a bail extending across the side of said flexible tubing opposite said stop, said spring being mounted to press said bail against said tubing to collapse and close said tubing against said stop by the force of said spring, said bail on collapsing said tubing pinching said tubing and effecting a displacement of a small amount of treatment material.

4. A dental prophylaxis apparatus as set forth in claim 3 including fluid pressure means for releasing said bail from said tubing, and a remote actuating means for controlling the flow of fluid to said pressure means.

5. A dental prophylaxis apparatus as set forth in claim 1 including conduit means mounted on said handpiece and terminating in discharge tips directed toward the zone of said cup, and remote control means for supplying water to one of said conduits and air to the other of said conduits whereby the treatment may be effected by the use of said rotatable cup and treatment material and the area of treatment thereafter washed by application of flushing water and dried by air without requiring removal of the head of the handpiece from the patient's mouth.

6. A dental prophylaxis apparatus as set forth in claim 5 wherein said handpiece comprises a removable end portion comprising said means for supporting said flexible applicator cup and wherein said conduits are drawn apart and separated on longitudinal movement of said portion away from said handpiece and said fluid line is similarly detachable and removable, the fluid line on said end portion having a portion of reduced diameter for engagement with the portion thereof on the handpiece and said water conduit having a similar but longer portion of reduced section whereby said end portion of the handpiece may be rotated after release from the main portion of the handpiece and said longer reduced portion inserted in said water supply conduit for directing water through said treatment material supply for flushing the fluid supply line on said detachable tip portion.

7. A dental prophylaxis apparatus as set forth in claim 5 including a single foot operated control unit including said quick acting means for selectively actuating and controlling said water supply means and said air supplying means and said means for selectively opening and closing said valve.

8. A dental prophylaxis apparatus as set forth in claim 1 wherein said compressible chamber reservoir comprises a removable cartridge having a piston therein and a charge of treatment material, and means for connecting the discharge end of said cartridge to said fluid line and the opposite end of said piston to said pressure amplifying means.

9. A dental prophylaxis apparatus as set forth in claim 1 wherein the means for rotating the flexible applicator comprises a motor mounted within said handpiece, and a remote foot controlled means for selectiively actuating said motor and said water supply means and said quick acting means for opening and closing said valve.

10. A dental prophylaxis apparatus of the type having a handpiece including means for supporting a rotatable flexible applicator cup and means for supplying fluid treatment material to the interior of the applicator cup a control system comprising:
    drive means for rotating said cup;
    means connectable to a water supply for receiving water and for amplifying the pressure thereof and having an outlet for the discharge of high pressure water;
    a compressible chamber reservoir for holding a supply of treatment material therein;
    a fluid line for conducting treatment material from said reservoir to the interior of the applicator cup;
    a normally closed valve in said fluid line;
    means connected to the outlet of said amplifying means for utilizing high pressure water for compressing said chamber and forcing treatment material into said line;
    manually controlled quick acting means for selectively opening and closing said valve for intermittent short periods to charge the applicator cup with selected amounts of fluid treatment material;
    said pressure amplifying means comprising a cylinder having a reciprocable piston therein, a concentric cylinder of reduced diameter extending from said first cylinder and a second piston secured to and extending from said first piston and reciprocable in said second cylinder, said second cylinder having an inlet in the side wall thereof and a water outlet in the end wall thereof, said side wall having an annular recess communicating with said inlet, an O-ring gasket in said recess, said gasket acting as a check valve for closing said inlet on the pressure stroke of said piston, and means for admitting fluid under pressure to said first cylinder for forcing said first piston towards said second cylinder whereby water is forced out under pressure through the outlet of said second cylinder.

11. A handpiece for dental prophylaxis apparatus including a hollow stationary shaft, an applicator cup support rotatably mounted on said shaft, means for rotating said support about said shaft, said support having a cup attaching means near its outer end and said shaft extending beyond said attaching means, a conical outwardly flaring flexible prophylaxis cup having a base provided with a recess for receiving said attaching means and a cylindrical center passage for receiving the end of said hollow shaft and for conducting fluid from said shaft, said center passage extending beyond the end of said shaft and having a smaller diameter than the external diameter of said shaft whereby the wall of said passage tends to close about and beyond the end of said shaft, said cup being rotatable about the end of the shaft and sealing the bearing surface of said support against the admission of treatment material thereto, the contraction of said central passage beyond said shaft upon distortion of said cup during use maintaining the sealing engagement of said cup and said shaft.

12. A handpiece head for dental prophylaxis apparatus as set forth in claim 11 including a slinger ring mounted on said support and spaced axially from said cup attaching means on the side thereof remote from said cup.

13. In a dental prophylaxis apparatus of the type having a handpiece including means for supporting a rotatable flexible applicator cup and means for supplying fluid treatment material to the interior of the applicator cup, a control system comprising:
    drive means for rotating said cup;
    means connectable to a water supply for receiving water from the supply and having an outlet for the discharge of high pressure water;
    a discardable cartridge of cylindrical configuration having a piston therein adjacent one end and being filled with treatment material between said piston and the other end thereof;
    a fluid line for conducting treatment material to the interior of the applicator cup;
    means for receiving said cartridge and for connecting the interior of said cartridge with said water pressure outlet at said one end and to said fluid line at said other end;
    means utilizing said high pressure water for forcing material for intermittent short periods from said cartridge to charge the applicator cup with fluid treatment material; and
    a single foot operated control unit for selectively actuating and controlling said drivve means and said means for utilizing said high pressure water to charge said applicator cup.

14. A dental prophylaxis apparatus as set forth in claim 13 including pressure amplifying means for amplifying the pressure of water from said water receiving means, said outlet communicating with and supplying water from said pressure amplifying means.

15. A dental prophylaxis apparatus of the type having a handpiece including means for supporting a rotatable flexible applicator cup and means for supplying fluid treatment material to the interior of the applicator cup, a control system comprising:
    drive means for rotating said cup;
    means connectable to a water supply for receiving water from the supply and having an outlet for the discharge of high pressure water;
    a removable cartridge for holding a supply of treatment material therein;
    a fluid line for conducting treatment material from said cartridge to the interior of the applicator cup;
    means including a piston connected to said outlet for the discharge of high pressure water for compressing said cartridge and forcing treatment material into said line;
    means for applying said high pressure water to said piston for intermittent short periods to charge the applicator cup with fluid treatment material;
    a single foot operated control unit for selectively actuating and controlling said means for applying said high pressure water to said cartridge and said drive means;

said apparatus including pressure amplifying means for amplifying the pressure of water from said waater receiving means, said outlet passing from said pressure amplifying means; and said pressure amplifying means comprising a cylinder having a reciprocable piston therein, a concentric cylinder of reduced diameter extending from said first cylinder and a second piston secured to and extending from said first piston and reciprocable in said second cylinder, said second cylinder having an inlet in the side wall thereof and a water outlet in the end wall thereof, said side wall having an annular recess communicating with said inlet, an O-ring gasket in said recess, said gasket acting as a check valve for closing said inlet on the pressure stroke of said piston, and means for admitting fluid undeer pressure to said first cylinder for forcing said first piston towards said second cylinder whereby water is forced out under pressure through the outlet of said second cylinder.

16. In a prophylaxis treatment dental handpiece of the type including a stationay cylindrical tube for delivering a supply of fluid treating material to the interior of a flexible applicator cup rotatable with respect to the tube, the improvement which comprises an applicator fittiing mounted for rotation on said tube, the outer wall of said tube constituting a bearing surface, a flexible applicator cup constructed to be mounted on said fitting, and means for utilizing a portion of the flexible applicator cup mounted on said fitting for providing a rotating seal between the end of said tube and said applicator cup and for preventing radially outward movement of fluid between said applicator cup and said tube toward the bearing surface on the outer wall of said tube.

17. In a prophylaxis treatment dental handpiece of the types including a stationary cylindrical tube for delivering a supply of fluid treating material to the interior of a flexible applicator cup rotatable with respect to the tube, means including a cup driving fitting rotatable about said tube for rotating said cup and for retaining the applicator cup about the end of said tube, said tube extending beyond said fitting, and means for providing between said tube and said applicator both a cylindrical seal about the outside of said tube and a radial seal on the end face thereof whereby fluid is prevented from moving outwardly over the end of said tube and into thee cylindrical seal.

18. The invention of claim 16 wherein said tube is formed with a relatively sharp angled shoulder around its outer circumference and said applicator cup is constructed with an axial bore having a diameter less than the outer diameter of said tube and longer than the extension of said tube beyond said fitting whereby said applicator cup when mounted on said fitting is compressed about the end of said tube.

19. The invention of claim 18 wherein the end face of said tube is flat and lies in a plane normal to the axis of the tube, said shoulder being of right angled configuration, and wherein said rotating seal is formed by face engagement of a radially extending flat portion of the wall of said bore with said end face of said tube.

20. In a prophylaxis treatment dental handpiece of the type including a stationary cylindrical tube for delivering a supply of fluid treating material to the interior of a flexible applicator cup and a driving member rotatable about said tube and having a cup attaching element thereon and said tube extending beyond said driving member, the method of forming an effective rotating seal between the tube and the cup which comprises:

providing the cup with a central axial bore longer than the portion of said tube extending beyond said member and having a diameter less than the outside diameter of said tube;

mounting the cup on the fitting with the wall of the bore compressed about the end of the tube; and while keeping the wall of the bore dry, rotating the cup about the tube to wear an annular sealing surface in the wall of the bore adjacent the end of said tube.

21. The invention of claim 16 including means effective upon the application of axial pressure on said cup in a direction toward said fitting for increasing the tightness of the seal between the end of said tube and said applicator cup.

22. The invention of claim 21 wherein said applicator cup comprises a thick base portion for mounting on said fitting and a cupped portion extending axially therefrom, and wherein said last mentioned means utilizes the transmission of forces through said cupped portion during use of said applicator and for effecting said increasing of the tightness of said seal.

23. As an article of manufacture, a dental prophylaxis material applicator for use on dental handpieces having means for delivering prophylaxis material through the handpiece, said applicator comprising a body of resilient highly flexible material having an end portion constructed for attaching the applicator to a rotary drive member and an adjacent thick central hub portion and a thick walled cup shaped portion concentric with said hub and extending axially therefrom, said hub portion having a central cylindrical passage extending therethrough and opening into said cup portion, said cup shaped portion being constructed to transmit to said hub portion pressure exerted axially against said applicator from the open end of the cup toward said hub portion, said hub portion being constructed to be rotated about a fixed shaft pressed into said passage, whereby when a shaft extends only partway through said passage, a seal is provided at the shaft end and pressure exerted axially on the cup will tend to close the passage adjacent the end of the shaft and increase the sealing effect.

24. The invention as set forth in claim 23 wherein said cup is of conical configuration and has its walls tapering from said hub toward the outer edge of the cup.

25. A dental prophylaxis apparatus as set forth in claim 8 wherein said connecting means includes a reciever mounted on said handpiece and comprising a shell closed at one end for receiving said cartridge and a detachable closure member at its other end, piercing tubes mounted in said closed end and in said closure member, said cartridge having piercible ends, and said piercing tubes being positioned for engagement with respective ends of said cartridge and upon pressing said detachable member into position to close said shell said piercing tubes both being forced through said cartridge ends to connect the discharge end of said cartridge to said fluid line and the piston end to said pressure amplifying means.

26. A dental prophylaxis apparatus as set forth in claim 13 wherein said connecting means includes a receiver mounted on said handpiece and comprising a shell closed at one end for receiving said cartridge and a detachable closure member at its other end, piercing tubes mounted in said closed end and in said closure member, said cartridge having piercible ends, and said piercing tubes being positioned for engagement with respective ends of said cartridge and upon pressing said detachable member into position to close said shell said piercing tubes both being forced through said cartridge ends to connect the discharge end of said cartridge to said fluid line and the piston end to said pressure amplifying means.

27. In a dental prophylaxis apparatus of the type having a handpiece including means for supporting a rotatable flexible applicator cup and means for supplying prophylaxis treatment material to the interior of the applicator cup, a control system for facilitating uninterrupted prophylaxis treatment which comprises:

drive means for rotating the applicator cup;
 reservoir means for holding a quantity of treatment material;
 a fluid line for conducting treatment material from said reservoir means to the interior of the applicator cup;
 means utilizing fluid pressure for forcing treatment material from said reservoir means through said fluid line to the interior of the applicator cup;
 means connectable to a fluid pressure supply for admitting fluid under pressure to said fluid pressure utilizing means; and
 foot controlled means for selectively actuating said drive means to rotate the cup and for effecting operation of said fluid pressure utilizing means to deliver desired quantities of treatment material to the cup, whereby the opeerator's hands are completely free to manipulate the handpiece without interruption and the applicator cup need not be removed from the patient's mouth for material supply purposes.

* * * * *